United States Patent [19]

Sato et al.

[11] 4,142,399

[45] Mar. 6, 1979

[54] METHOD FOR AUTOMATIC QUANTITATIVE MEASUREMENT OF HYDROGEN IN A METAL AND AN APPARATUS FOR CARRYING OUT SAID METHOD

[75] Inventors: Hideshi Sato, Tokyo; Takashi Otsubo, Machida; Syunsuke Goto; Minoru Amano, both of Sagamihara; Naoyuki Seriu, Machida, all of Japan

[73] Assignee: Nippon Steel Corporation, Tokyo, Japan

[21] Appl. No.: 808,357

[22] Filed: Jun. 20, 1977

[30] Foreign Application Priority Data

Jun. 19, 1976 [JP] Japan .................................. 51/71701
Mar. 8, 1977 [JP] Japan .................................. 52/24406

[51] Int. Cl.² ........................ G01N 7/14; G01N 31/00
[52] U.S. Cl. ........................................................ 73/19
[58] Field of Search .................................. 73/19, 23.1

[56] References Cited

U.S. PATENT DOCUMENTS

| | | | |
|---|---|---|---|
| 3,427,863 | 2/1969 | Schultz | 73/19 |
| 3,498,105 | 3/1970 | Hetherington | 73/19 |
| 3,500,675 | 3/1970 | Sandstede et al. | 73/19 |
| 3,517,543 | 6/1970 | Gasser | 73/19 |
| 3,557,604 | 1/1971 | Baecklund | 73/19 |
| 3,562,501 | 2/1971 | Mears | 73/23.1 |
| 3,905,222 | 9/1975 | Boillot | 73/19 |

*Primary Examiner*—Stephen A. Kreitman
*Attorney, Agent, or Firm*—Wenderoth, Lind & Ponack

[57] ABSTRACT

Hydrogen in a metal, particularly in a welded metal, can be quantitatively measured by a simple apparatus using sequence control or computer control.

The lower limit of hydrogen to be measured according to this invention is much lower yet is more accurate as compared with the prior mechanism of this field.

4 Claims, 4 Drawing Figures

METHOD FOR AUTOMATIC QUANTITATIVE MEASUREMENT OF HYDROGEN IN A METAL AND AN APPARATUS FOR CARRYING OUT SAID METHOD

DETAILED DESCRIPTION OF THE INVENTION:

This invention relates to a method for quantitatively measuring hydrogen in a metal and an apparatus for effecting said method. More particularly, it relates to a method and an apparatus for quantitatively measuring hydrogen existing in a slight amount in a deposited metal obtained by welding in a simple, accurate and automatic manner.

Recently, efforts have been made to lower the amount of hydrogen in a deposited metal by the use of an improved welding rod and steel material for the purpose of preventing "weld-cracking" of a high tensile steel which is considered to have high sensitivity for weld-cracking. In order to accomplish this, it has been considered necessary to quantitatively measure a slight amount or 2ml/100g or less amount of hydrogen in a deposited metal with good accuracy. In case of measuring an amount of diffusible hydrogen in a deposited metal, it has heretofore been a practice in Japan to effect a method for measuring an amount of hydrogen in a deposited metal involving glycerin displacement according to JIS Z 3113-1975. On the other hand, a measuring method (Doc. II-A-275-70) of I.I.W. (International Institute of Welding) utilizing Mercury Displacement Method has widely been used in each country of the world.

Comparing the JIS method with the IIW method mentioned above, the former method has a great advantage in not using mercury which is harmful to the human body, while it has been reported that the measuring value of the former method is about 40% lower than that of the latter method. The reason for such lower value may be that since the floating velocity of hydrogen in small bubbles discharged into glycerin from a test piece is much slower than that in mercury (which is said to be about $1/10^4$), it can not float up fully within the collecting time of 48 hours, remaining as small bubbles in the glycerin. Another reason is pointed out to be that the hydrogen has some solubility, though small, in the glycerin. There are also factors for fluctuation such as errors caused by the collecting liquid, the test material, the welding conditions, the atmosphere, etc. The fluctuation "$\sigma$" caused by the above is about 0.5 ml/100g, and what is discriminable by repetition of n =4 is said to be about 1 ml/100g.

On the other hand, the IIW method has a fatal disadvantage in that a great deal of mercury which is harmful to the human body has to be handled. Moreover, it often happens that the air will invade into a measuring container through its joint parts during the preservation of such reduced pressure as $10^{-1}$ mmHg for 72 hours, which results in unsuccessful measurement. The fluctuation "$\sigma$" of measuring values obtained by the IIW method has been reported to be about 0.5 ml/100g, and the lower limit above which the quantitative measuring is possible is said to be about 2 ml/100g. This lower limit for the quantitative measuring can be determined by visual observation of the amount of gas collected in a burette having the minimum scale of 0.05 ml in view of the fact that the amount of deposited metal is about 1g.

On the other hand, not only the amount of hydrogen in the deposited metal but also the amount of hydrogen in the molten metal during welding may provide an important finding for clarifying the weld-cracking phenomenon. As a means to clarify the course of dissolution of hydrogen in the molten metal, Mr. G.R. Salter reported in British Welding Journal, June 1963, p. 316 to 325, a method including the step of melting a steel by arc in a closed container in which a mixture gas of argon and hydrogen has been filled; introducing the resulting molten steel into a separate chamber isolated from an arc chamber in said container immediately after the arc disappears; and, quantitatively measuring the amount of the hydrogen, by a thermal conductivity measuring unit, which has been discharged with the decrease of solubility of hydrogen due to the cooling solidification of the molten steel (the lapse time after disappearance of arc is 45 seconds at maximum).

According to said method, it is possible to quantitatively measure 0.2 to 1.2 ml (N.T.P.) of hydrogen per 3 to 9 g of material, that is, about 2 ml/100g to 12 ml/100g of hydrogen. In this case, the maximum error is said to be ±0.007 ml (about 0.1 ml/100g). From the standpoint as to whether or not the above method can be utilized in the quantitative measuring of hydrogen in the deposited metal mentioned above, it must be concluded that Mr. Salter's method is not suitable for the quantitative measuring of hydrogen in the deposited metal because this method has been developed only for mesuring a great deal, or 0.2 to 1.2 ml (2ml/100g to 12 ml/100g) of hydrogen discharged for such short time as about 45 seconds after the disappearance of arc.

As set forth hereinabove, all three methods cannot meet the conditions required in the measuring of a minor amount of hydrogen in the deposited metal with respect to the lower limit and the accuracy for quantitative measuring, in addition to the aforesaid disadvantages.

When it is desired to obtain the amount of residual hydrogen, the diffusible hydrogen is measured either by the JIS method or by the IIW method and then the same test piece is cut, cleaned and dried, which is thereafter subjected to the quantitative measuring by the use of another quantitative measuring unit for hydrogen in a steel.

It is, however, very cumbersome to measure the amount of the diffusible hydrogen and the residual hydrogen in the same test piece by the use of the different apparatus and the different operations, respectively.

It is, therefore, an object of this invention to overcome all the disadvantages as mentioned above.

It is another object of this invention to provide a method and an apparatus for quantitatively measuring the amount of the diffusible hydrogen and the residual hydrogen existing in a slight amount in metal automatically and with excellent accuracy.

According to this invention, there is provided a method for automatically and quantitatively measuring hydrogen in a metal which comprises providing a hydrogen collector in a system for quantitatively measuring hydrogen through which a carrier gas is always passed; allowing a diffusible hydrogen to be discharged into said collector from a test piece placed in said collector for a predetermined time; introducing said hydrogen into a gas analysing unit by means of said carrier gas whereby quantitative measuring is conducted; repeating the above-stated steps any desired number of times, while setting the time per analysis cycle and the cycle number and conducting the necessary valve operation, quantitative measuring operation and recording operation by means of sequence control, and quantitatively measuring the diffusible hydrogen.

According to this invention, there is still provided a method for automatically and quantitatively measuring hydrogen in a metal which comprises providing a hydrogen collector in a system for quantitatively measuring hydrogen through which a carrier gas is always passed; preserving a test piece in said collector for a given predetermined time; introducing a hydrogen discharged therefrom into a gas analysing unit by means of said carrier gas whereby a quantitative measuring is conducted; repeating the above stated steps any desired times so as to quantitatively measure the discharged hydrogen, and setting the time per analysis cycle and the cycle number and conducting the necessary valve operation, quantitative measuring operation, recording operation and data-processing operation by means of computer control.

According to this invention there is also provided a method for automatically and quantitatively measuring hydrogen in a metal which comprises providing a hydrogen collector in a system for quantitatively measuring hydrogen through which a carrier gas is always passed; preserving a test piece in said collector for a given predetermined time and at a given predetermined temperature; introducing a hydrogen discharged therefrom into a gas analysing unit by means; of said carrier gas whereby a quantitative measuring is conducted; repeating the above stated steps any desired times so as to quantitatively measure the hydrogen discharged in equilibrium at said temperature, and setting the heating extraction temperature, the time per analysis cycle and the cycle number and conducting the necessary valve operation, quantitative measuring operation, recording operation and data-processing operation by means of computer control.

According to this invention, there is additionally provided an apparatus for carrying out the above methods.

In the practice of this invention, a slight amount of hydrogen which is as low as 2 ml/100g or less can be quantitatively measured with good accuracy and moreover it is possible to grasp the behavior of a slight amount of discharged hydrogen which is in the order of $10^{-5}$ ml/5 min. or $10^{-5}$ ml/hr.

This invention is further described below with respect to the drawing.

Figure 1:
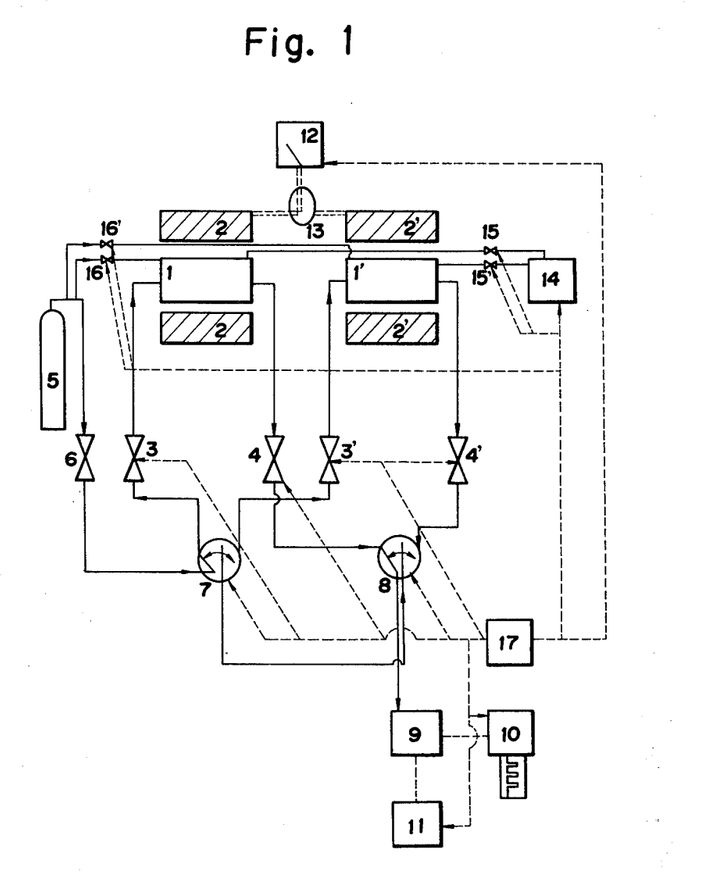
FIGS. 1 and 2 are schematic views illustrating the respective embodiments of the apparatus for carrying out the method of this invention.

In FIG. 1, the numeral 1 is a hydrogen collector or a container for collecting hydrogen discharged from a test piece contained therein. It is designed such that it can be kept in a heating furnace 2 capable of controlling the temperature by means of a temperature-indicating and adjusting unit 12 via a change-over switch 13. The collector 1 is connected to the gas-flowing path of a hydrogen quantitiative measuring system via an inlet valve 3 for introducing a carrier gas and an outlet valve 4 for taking out the collected hydrogen. As for the carrier gas, Ar gas or $N_2$ gas, etc. may be used. The carrier gas is supplied from a bomb 5 while it is subjected to a flow adjustment by a valve 6 for controlling the amount of flowing. The numerals 7 and 8 are change-over switches for changing the flowing path for the carrier gas to the collector 1 or 1'. The valve 7 and the valve 8 are connected to the side of the inlet valve 3 and to the side of the outlet valve 4, respectively. The valve 8 is intended for leading the hydrogen to a gas analysing unit 9 which has been collected in the collector 1 or 1' and carried by the carrier gas. Said unit 9 is connected to a recorder 10 for analog-recording the measuring value obtained by the quantitative analysis as the analysis data recording means, and to an integrator 11 for recording the integrated amount of the measuring valves. The collector 1 is provided with pipes such that it is possible to exhaust gases via a valve 15 by means of a vacuum exhausting unit 14. There is also a valve 16 intervening between the bomb 5 and the collector 1 for shutting off the bomb 5 when the collector 1 is exhausted to vacuum.

The sequence control unit 17 hereinafter explained in detail is intended to carry out the above mentioned controls, i.e., the control of the heating time and temperature in the heating furnace 2, the control of the time for collecting the hydrogen gas in the collector 1, the control of the flowing path and the timing of the carrier gas for carrying the hydrogen gas collected in the collector 1 to the gas analysing unit 9, the control of start and stop of the operations of the recorder 10 and the integrator 11 in response to the time of introducing a sample gas from the collector 1 to the gas analysing unit 9, and the control of the vacuum exhausting unit 14 and the valves 15 and 16 for exhausting the collector 1 and introducing the carrier gas thereinto for the purpose of the quantitative measuring of the residual hydrogen.

In the embodiment of the apparatus as stated hereinabove, it is necessary to have the collector, the gas analysing unit, means to record the analysis data and the sequence control mechanism, in addition to the carrier gas. Moreover, when extracting the hydrogen at high temperature, it is further necessary to have the heating furnace, the temperature control unit therefor and the vacuum exhausting unit. It is possible to change or modify the arrangement of the valve and the piping system as the case may require. In FIG. 1, other collecting groups of the same structure are expressed as 1', 2', 3', 4', etc., but it is, of course, possible to provide more groups of a similar structure in addition to those indicated. In such a case, the temperature control of the respective heating furnaces is carried out by said change-over switch 13.

As for the material to be used for the collector 1, it is necessary that it does not allow the hydrogen to permeate therethrough and that its internal dead space is not more than about 100 ml. In case that the hydrogen is allowed to be discharged from a test piece at high temperature, the material of the container should have a full strength at temperatures up to 1300° C. and should not allow the hydrogen to permeate therethrough. It is also desirable that the internal dead space be about 100 ml or less. As for the heating furnace 2, it is necessary to select one which can be heated up to about 1300° C. or more. It is possible to use an ordinary one as the temperature-indicating and adjusting unit.

It is required that the gas analysing unit 9 can quantitatively measure the hydrogen carried by the carrier gas to the extent of at least $1 \times 10^{-5}$ ml (N.T.P.), and thus a gas chromatograph of thermal conductivity detection type may be used therefor. The integrator 11 should preferably be one capable of integrating the analysis peak of the subject gas only without suffering from the noise, etc. caused by the fluctuation of the base line incidental to the long-time operation of the gas analysing unit 9 or the fluctuation of pressure incidental to the opening or closing of the valve for carrying the carrier gas. It is thus desirable to use a digital integrator, for example, to be used for gas chromatograph.

As for the analog recorder, it may be, for example, an ordinary pen recorder. The vacuum exhausting unit 14 should be capable of exhausting to vacuum to the extent of at least $10^{-1}$ mmHg. The sequence control unit 17 should be such that the starting switch for actuating valves or switches, etc. can effect operations of "connection" or "shutting-off", and thus it may be, for example, a type of pin board programming system.

Figure 2:
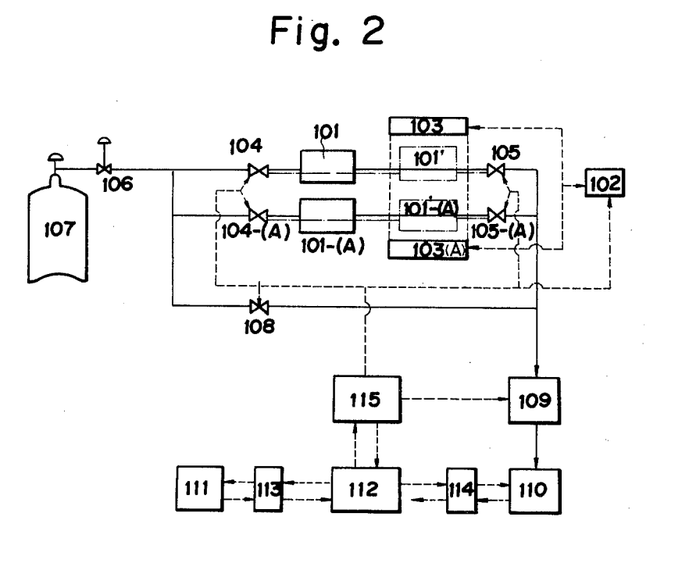

In FIG. 2, the numeral 101 is a collector or a container in which a test piece is placed and a hydrogen gas discharged at a given predetermined temperature is collected. It is designed such that it can be preserved in a heating furnace 103 as required, and the temperature of said furnace can be controlled by means of a temperature-indicating and adjusting unit 102. The collector 101 is connected to the gas flowing path in the hydrogen quantitative measuring system via an inlet valve 104 for introducing the carrier gas and an outlet valve 105 for taking out the carrier gas and the collected hydrogen. As the carrier gas, Ar gas, $N_2$ gas, etc. may be used. The carrier gas is supplied by a bomb 107 while subjected to adjustment of the flow rate by means of a flow rate adjustment valve 106. The collected hydrogen is led to a gas analysing unit 109 by the carrier gas. The carrier gas is allowed to flow directly to the gas analysing unit 109 via a carrier gas valve 108 except for the period during which the hydrogen gas collected in the collector 101 is carried. The analysing unit 109 is connected to an integrator 110 for calculating the integrated amount of the hydrogen gas measuring peak. the numeral 112 is a control part of the computer. Said control part 112 conducts the control of the collecting time and time interval for collecting the hydrogen in the collector 101; the control of the heating temperature, time and cycle for the test piece in the heating furnace 103; the control of the timing of selection and switch of the flow path of the carrier gas for sending the sample gas collected in the collector 101 to the gas analysing unit 109; the control of the start and stop of operation of the integrator 110 at the time when it is not hindered by the pressure fluctuation noise and the measuring peak caused by other gas component and in response to the time when the sample gas is introduced from the collector 101 to the gas analysing unit 109. Moreover, it conducts the recording of the measuring values by means of the gas analysing unit 109 via a data input and output unit 111, as well as the data processing for providing the arranged analysis data based on the stored measuring values as the analyst may desire. The numeral 113 is an interface for controlling the input and output; 114 is an interface for controlling the integrator; and 115 is an interface for controlling the apparatus. The numeral 101' indicates the condition under which the collector 101 is preserved in the heating furnace 103. The numerals 101-(A), 101'-(A) and so on examples of units of the same structure. It is thus possible, of course, to provide a plurality of sets of similar units in addition to those shown.

The collector 101 used in the apparatus shown should have the material which does not allow the hydrogen to permeate therethrough and its internal dead space is preferably about 100 ml or less. In case of, for example, melting the test piece to cause the hydrogen to be discharged therefrom, it is necessary that the collector 101 be provided with a heat-resisting crucible made of graphite, berillium oxide, etc. and that the material thereof has a sufficient strength and does not allow the hydrogen to permeate therethrough even if the sample in the crucible is heated up to about 2500° C. Also it is preferable that the internal dead space be not more than about 100 ml. The heating furnace 103 should be designed so that it can heat the test piece to any desired temperature up to about 2500° C. and thus may be a high-frequency furnace or a laser furnace, etc. As for the temperature-indicating and adjusting unit 102, it may be that of a type wherein the measuring values obtained in the ordinary thermocouple thermometer or the two-color-eye pyrometer are fed back to the output of the heating furnace.

The gas analysing unit 109 should be such that it can quantitatively measure the hydrogen carried by the carrier gas to the extent of at least $1 \times 10^{-5}$ ml (N.T.P.) and thus it may be a gas chromatograph of thermal conductivity detection type, for example. The integrator 110 should preferably be of a type capable of integrating the analysis peak of the object hydrogen only, without suffering from the quantitative measuring noise, etc. caused by the fluctuation of the base line incidental to the long-time operation of the gas analysing unit 109 and the fluctuation of the pressure incidental to the opening and closing of the valve for carrying of the carrier gas. Accordingly, it may preferably be a digital integrator for gas chromatograph, for example. The data input and output unit 111 may be an ordinary data typewriter to be used for a computer. The computer control part 112 should be designed such that it can control the data input and output unit 111, the integrator 110, the valves 104, 105, 108, the gas analysing unit 109, the temperature-indicating and adjusting unit 102 and the heating furnace 103, respectively, via the interfaces 113, 114 and 115. It is also necessary that said part can effect sorting of about fifty thousand (50,000) analysis data. It may thus be an ordinary personal micro-computer.

An example of using the apparatus of FIG. 1 for carrying out this invention is described below.

A test piece is prepared according to the ordinary method for preparation of a test piece, for example, the IIW method for effecting the analysis of Doc. II-A-275-70,6.1. The test piece is placed into the collector 1 preserved in the heating furnace 2, and the air inside the collector 1 is purged by the carrier gas if necessary. The inlet valve 3 and the outlet valve 4 are closed. When the inlet valve 3 and the outlet valve 4 are closed, only the carrier gas is led to the analysing unit 9 by means of the inlet switch valve 7 and the outlet switch valve 8. The sequence control unit 17 works so as to open the inlet valve 3 and the outlet valve 4 after lapse of any given set time and operate the inlet switch valve 7 and the outlet switch valve 8 so that the hydrogen discharged from the test piece and stored in the collector 1 may be led to the analysing unit 9 by the carrier gas coming from the carrier gas bomb 5 via the valve 6.

The sequence control unit 17 operates both the recorder 10 and the integrator 11. The amount of hydrogen in the collector 1 is recorded by the recorder 10 as the analog signal or by the integrator 11 as the integrated digital amount after correction of the fluctuation of the base line. After the analysis is over, the sequence control unit 17 closes again the inlet valve 3 and the outlet valve 4 and actuates the inlet switch valve 7 and the outlet switch valve 8 so as to lead only the carrier gas to the gas analysing unit 9. The time from the opening of the inlet valve 3 to the starting of operation of the integrator 11 is preliminarily set. After elapse of the given set time, the sequence control unit 17 again repeats the same analysis cycle, whereby the amount of hydrogen discharged in the collector 1 after the first analysis is measured quantitatively. Any given number of this analysis cycle which has been set in the sequence control unit 17 is repeated, and the operation of the quantitative measuring of diffusible hydrogen at room temperature is finished. In this case, the extracting time may be, in principle, 72 hours according to the IIW method. The sum of the hydrogens obtained by each analysis cycle will give the amount of the "room temperature" diffusible hydrogen.

Figure 3:
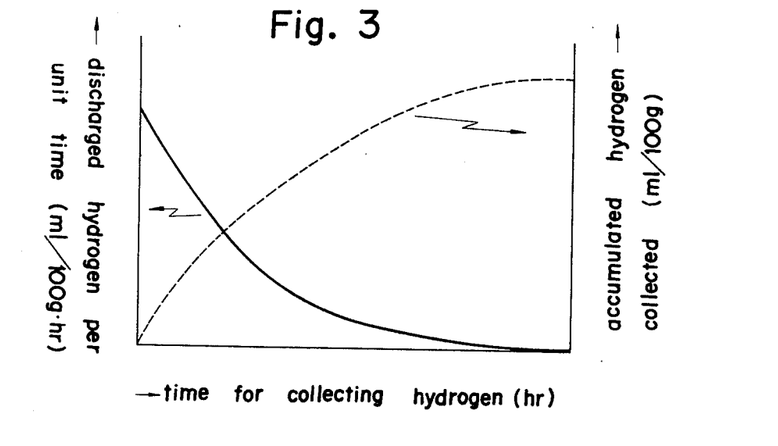
FIGS. 3 and 4 are examples of the graphs showing the amount of hydrogen with respect to the collecting time and the heating temperature, respectively.
Figure 4:
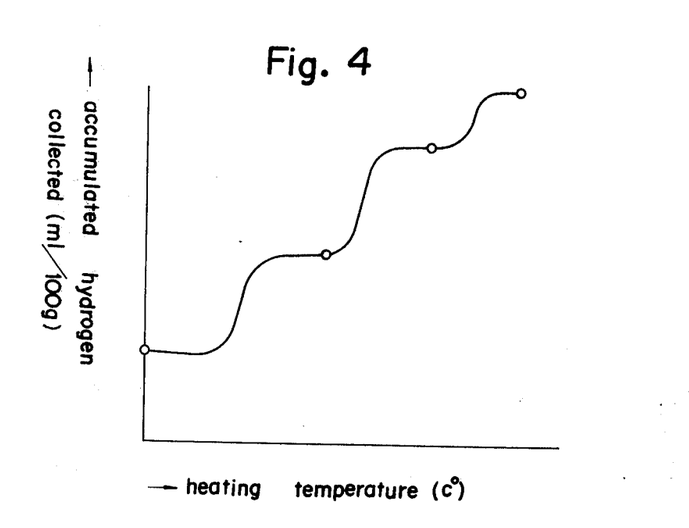

Then the vacuum exhausting unit 14 is actuated to open the valve 15 and exhaust the collector 1, and the valve 15 is again closed. The temperature-indicating and adjusting unit 12 is actuated to elevate the temperature of the heating furnace 2 to any temperature below 1300° C. so as to indirectly heat the test piece in the collector 1 whereby the residual hydrogen is allowed to be discharged for a given predetermined time. Thereafter, the valve 16 is opened to introduce the carrier gas. After the pressure is increased to the normal pressure; the valve 16 is closed again. Then the inlet switch valve 7 and the outlet switch valve 8 is actuated to open the inlet valve 3 and the outlet valve 4 whereby the hydrogen discharged at high temperature is led to the gas analysing unit 9 by the carrier gas. As is the case with the above mentioned "room temperature" discharged hydrogen, the "high temperature" discharged hydrogen can also be recorded in analog or digital amount. In this case it is also possible to conduct "fractional" quantitative measuring of the residual hydrogen per each extracting temperature by setting the heating temperatures in any given stages. In connection with the foregoing operation, it is possible to obtain the similar measuring values of two test pices for the same operation time, which can be done in the same sequence control by operating, for example, the collector 1', the heating furnace 2', the inlet valve 3' and the outlet valve 4' and leading the hydrogen coming from the collector 1' to the gas analysing unit 9 when the hydrogen coming from the collector 1 is not being analysed by the gas analysing unit 9. Consequently, as mentioned above, if plural sets of extracting units of the similar construction are provided, it is possible to conduct quantitative measuring of the diffusible hydrogen and the residual hydrogen in the plural number ($n \geq 2$) of test pieces to the slightest amount with good accuracy by means of the method described above. Furthermore, it is also feasible, as the case may require, to obtain a useful, "microscopical" measuring value, such as the amount of hydrogen discharged per unit time (see FIG. 3) or the amount of hydrogen extracted per each heating temperature with respect to the residual hydrogen (see FIG. 4).

If the amount of hydrogen discharged per unit time or the amount of hydrogen extracted per each heating temperature as stated is not necessary, only the aimed measuring value may be obtained by simplifying the analysis operation, of course. The example of apparatus shown in FIG. 1 is shown to be only one mode of working of the invention. Thus any changes or modification can be done without departing from the spirit of this invention such, for example. as use of the mass spectrometer instead of the gas chromatograph or the cam programmer instead of the pinboard programmer. If the quantitative measuring of the residual hydrogen is not particularly required, it is of course possible to omit the apparatus and operation associated therewith.

An example of using the apparatus of FIG. 2 to carry out the method of this invention is described below.

A test piece is prepared according to an ordinary method for preparing the test piece such as IIW method (Doc. II-A-275-70, 6.1 analysis). The test piece is placed in the collector 101 preserved in the heating furnace 103. After the air inside the collector 101 is purged, if necessary, by the carrier gas, the inlet valve 104 and the outlet valve 105 are closed. When these valves are being closed, the valve 108 for the carrier gas is opened so as to lead only the carrier gas to the gas analysing unit 109. After lapse of any predetermined set time, the computer control part 112 opens the inlet valve 104 and the outlet valve 105 via the interface 115 while closing the carrier gas valve 108 whereby the hydrogen discharged from the test piece and stored in the collector 101 is led to the gas analysing unit 109 by the carrier gas coming from the bomb 107 via the valve 106. The said part 112 also actuates the integrator 110. The amount of hydrogen in the collector 101 is quantitatively measured as the analog amount by the gas analysing unit 109. The integrated digital value after corrected with respect to the baseline fluctuation by the integrator 110 is passed to said part 112 via the interface 114. The integrated digital value is converted into the amount of hydrogen by the computer control part 112 using the formula concerning the relation of the preliminary stored integrated digital value and the amount of hydrogen, and "printed out" via the interface 113 by means of the input and output unit 111 with the affixed index such as test number, analysis number, etc. After the analysis is over, the part 112 works to close the inlet valve 104 and the outlet valve 105 of the collector 101 via the interface 115 and open the carrier gas valve 108, through which only the carrier gas is led to the gas analysing unit 109. The time from the opening of the inlet valve 104 to the starting of operation of the integrator 10 is preliminarily stored in the control part 112. After lapse of a given set time, the part 112 again repeats the similar analysis cycle with respect to the collector 101-(A) in which another test piece has been placed. Then after lapse of a given set time the part 112 repeats again the similar analysis cycle with respect to the collector 101, where the amount of hydrogen newly discharged after the first analysis is measured quantitatively. With respect to the collector 101 and the collector 101-(A), this analysis cycle is repeated any desired times stored in the control part 112. The operation of the quantitative measuring of the "room temperature" diffusible hydrogen is thus completed. In this case, the extracting time may be, in principle, 72 hours according to the IIW method.

Then the collector 101 is preserved in the heating furnace 103, the temperature of which has been adjusted at a given predetermined temperature below 2500° C. by means of the temperature-indicating and adjusting unit 102. The temperature is allowed to elevate for a given predetermined time and the hydrogen discharged is led to the gas analysis unit 109 in a similar manner whereby the quantitative measuring value is output via the control part 112. In this case it is required that the integrated digital value is converted to the amount of hydrogen according to the relationship which has been already made up under the same heating temperature of the furnace and stored. The amount of hydrogen is also measured similarly with respect to the collector 101-(A). In this case, it is also possible to conduct fractional quantitative measuring of the residual hydrogen per each extracting temperature by setting the heating temperatures in desired plural stages.

The amount of hydrogen which has been quantitatively measured by the above operations alternately with respect to the collector 101 and the collector 101-(A) is output via the input and output unit 111, according to the data processing system preliminarily stored and to the computer control part 112, and if desired, after being converted into the integrated value at each quantitative measuring time or the quantitative measuring value arranged in time-line of each collector.

With respect to the above mentioned operation, it is possible that, by the same computer control and when the hydrogen from the collector 101 or from the collector 101-(A) is not being analysed by the gas analysing unit 109, such other collectors not shown as 101-(B), 101-(C), ... 101-(N), such other inlet valves not shown as 104-(B), 104-(C), ... 104-(N), and such other outlet valves not shown as 105-(B), 105(C), ... 105-(N) are operated so as to lead to the unit 109 the hydrogen from the collector 101-(B), 101-(C), ... 101-(N), whereby the measuring values regarding a lot of test pieces can be obtained substantially for the same time and the measuring data arranged per each test piece can also be obtained.

In case that the amount of hydrogen discharged per each unit time or the amount of hydrogen extracted per each heating temperature is not necessary, it goes without saying that only the aimed measuring value may be obtained by simplifying the analysis operation.

The apparatus shown in FIG. 2 is only one of the modes of working of the invention, and any change or modification can be made without departing from the spirit of this invention. Thus, the mass spectrometer instead of the gas chromatograph, the radiation-type heating furnace instead of the high frequency heating furnace, the digital voltmeter instead of the integrator for gas chromatography, or the micro-processor plus memory circuit instead of the personal micro-computer can be used effectively to practice the invention.

The following is the examples of this invention.

EXAMPLE 1

A test piece is prepared according to the IIW method which is shown in the first column of Table 1. The welding is effected using the material shown in the third column according to the welding method shown in the second column of Table 1. The test piece thus prepared (the two pieces in the IIW are made one piece in this example and the size is changed to width 15 mm × length 15 mm × height 10 mm) is subjected to operations described with respect to FIG. 1, and measured at room temperature and one hour cycles by the use of a gas chromatography. This is repeated 48 times, and the total results of each are shown in the fourth column and the total results obtained by heat-extracting hydrogen at 1000° C. and analysing twice at 30 minutes cycle are shown in the fifth column. For reference, the results of measuring according to the IIW method are shown in the sixth column, while the results of measuring according to the JIS method are shown in the seventh column.

In Table 2 are shown the comparisons between the so-called lower detection limit of this invention and that of the IIW or JIS method, the reproducibility obtained by the results of Table 1 (which is calculated from $\bar{R}/d_2$ according to the conventional method by dividing into 3 groups according to the amount of hydrogen) of this invention and that of the IIW or JIS method, etc.

As is clear from these comparisons, the method of this invention has succeeded in lowering the lower detection limit of hydrogen one thousandth less as compared with the conventional IIW or JIS methods. Also considering the relative measuring value (ml/100 g) with the amount of sampling, and comparing the lower limits of the quantitative measuring in view of the overall reproducibility including even the mechanism of hydrogen invasion through the welding bead, it is seen that this invention can not only improve the conventional method extensively so as to make possible the quantitative measuring of the diffusible hydrogen of the low concentration region, but also give a more accurate value even of the trace concentration region.

EXAMPLE 2

Six test peices A, B, C, D, E and F having the shape of 9 mm dia. × about 14 mm length are cut out from a carbon steel. It is subjected to finish polishing by Emergy 600 to give the weight of 7,000 g. The hydrogen charging is conducted by cathode electrolysis of constant electric current in $1N-H_2SO_4$ solution to which 5 As has been added, with the opposite electrode of platinum wire in the current density of 500 mA/cm$^2$ for 1, 5, 10, 50, 100 and 500 minutes, respectively. Immediately after the charge, the test piece is placed in the collector 1 of FIG. 1 and the measuring is repeated 48 times at room temperature at one hour cycle. The total sums of the respective measuring values are shown in Table 3. The change in the amount of discharged hydrogen in the elapse of time with respect to the pieces D and F is shown in Table 4.

As is obvious from these results, even the trace amount of hydrogen in the order of 0.00013 ml or 0.00002 ml discharged for as short a time as 5 minutes or 10 minutes can automatically and quantitatively measured along the lapse of time in the practice of this invention. Moreover, even with respect to the total discharged amount obtained by summing up these amounts, the extremely small or trace amount of as low as 0.00056 ml of hydrogen can be measured in this invention, which amount could hardly be measured in the conventional method.

EXAMPLE 3

Four test pieces shown in the first column of Table 5 is prepared according to the IIW method. These are subjected to welding by the use of welding materials shown in the third column and by the use of welding methods shown in the second column, respectively. As controls, four test pieces made according to the IIW method are prepared, wherein two pieces according to IIW correspond to one piece of this example and the size is changed to 15 mm wide × 15 mm long × 10 mm high. The details of the quantitative measuring are as follows:

Ar gas is allowed to flow as the carrier gas at the flowing rate of 100 ml/mm. The electromagnetic valves are used respectively as the inlet valve 104, the outlet valve 105 and the carrier gas valve 108. As for the gas collecting container or collector 101, a transparent collector made of quartz having a graphite crucible for heating is used. A high frequency furnace for heating the graphite crucible is used as the heating furnace 103. A unit for controlling the output electric current of the high frequency heating furnace with the temperature measuring values obtained by the optical pyrometer of two-color-eye pyrometer is used as the temperature-indicating and adjusting unit 102. As the gas analysing unit 109, a gas chromatograph of thermal conductivity detection type is used. As the integrator 10, a dynamic range, and baseline correcting digital integrator is used, and as the data input and output unit 111, a keyboard input and unit and a thermal printer are used. As the computer control part 112, a 8K bite personal microcomputer is used, and as the interface 113 for input and output control, one manufactured by Yokogawa Hewlett-Packard Co. is used. As the interface 14 for integrator control, one made by Takeda Riken Co. is used while as the interface 115 for apparatus control, one of electromagnetic relay control type made by Nippon Steel Corporation is used. Each valve is operated such that the analysis time after opening the inlet valve 104 and the outlet valve 105 is 150 seconds; the waiting time before the integrating operation starts is 20 seconds; the integrating time is 70 seconds; and the time from take-out of hydrogen by opening of the inlet valve 104 and the outlet valve 105 to closing of the inlet valve 104 and the outlet valve 105 and opening of the carrier gas valve 108 is 70 seconds.

The measuring is conducted 48 times at room temperature and at one hour cycles. The total of the measuring values with respect to the respective samples is shown in the fourth column of Table 5; the total of the measuring values obtained by extracting at 500° C. and measuring three times at 15 minutes cycle is shown in the fifth column of Table 5; the total of the measuring values obtained by extracting at 1000° C. and measuring twice at 15 minutes cycle is shown in the sixth column of Table 5; and the total of the measuring values obtained by extracting at 2100° C. under molten condition of the sample is shown in the seventh column of Table 5.

For reference, the result of measuring according to the IIW method is shown in eighth column and that according to the JIS method is shown in the nineth column of said Table.

In Table 6, the comparisons with the reproducibility (calculated from $\bar{R}/d_2$ according to the ordinary method) obtained based on the results of measuring of Table 5 are shown. It is obvious from these comparisons that the method of this invention makes it possible to lower the absolute lower detection limit for hydrogen one thousandth less as compared with the conventional method such as the IIW or JIS methods, and improves extensively the conventional method, as comparing the lower limits for quantitative measuring indicated by the ml/100 g by taking into account the reproducibility of the over-all tests including the amount of sample taken and the hydrogen charge from the welding bead. It is thus possible to conduct accurate quantitative measuring in the low concentration range of the diffusible hydrogen. Moreover, in the practice of this invention, there is no need of providing a separate apparatus for the quantitative measuring of hydrogen discharged by heating or melting, and also there is no need of suffering from the error caused by the discharge of hydrogen incidental to the processing of the test piece for the quantitative measuring of the discharge of hydrogen by heating or melting. And yet it is possible in this invention to conduct, by the same apparatus the quantitative measuring of the amount of the heat-discharging hydrogen and of the melt-discharging hydrogen in addition to the amount of the room - temperature-diffusible hydrogen. Moreover, the calculation based on many measuring data should be required in order to reach the final data of this invention shown in the fourth to seventh columns of Table 5. For example, one datum shown in the fourth column in Table 5 can be obtained only by converting the measuring values (number: 4 × 48) into the amount of hydrogen (ml) using the calculation formula which has preliminarily been made up per each heat-extracting temperature; selecting therefrom only 48 measuring values of the hydrogen amount concerned with the aimed sample; summing up these; and then dividing the same by the weight of the sample.

In order to utilize the final data shown in the 4th to 7th column in Table 5, it takes about one week by usual manual calculation. It is possible to record the measuring values by punching a paper tape, and having a separate computer reading the same to effect the necessary data processing. However, it takes about half-a-day operation to punch the measuring values on the paper tape.

In the practice of this invention, however, it is possible to sum up the measuring values per each analysed sample immediately after all the measuring is over, converting the same into the amount of hydrogen and thereby obtaining the final data which has been converted into the discharged amount per unit weight.

As stated above, this invention makes it possible not only to accurately and automatically effect the quantitative measuring of the amount of diffusible hydrogen and that of melt-discharged hydrogen in plural metallic samples to the extent of as low as $1 \times 10^{-5}$ ml but also to automatically measure the change of the discharge velocity of the extremely slight amount (down to $1 \times 10^{-5}$ ml) of hydrogen discharged into the container per unit hours (its lower limit is three minutes), whereby the microscopical behavior of the hydrogen discharged can be clarified. It has also a prominent advantage that even when the measuring is conducted concurrently with respect to plural number of samples, the arranged data per each test piece can be given as soon as the measuring is over, which will contribute much to the safety of the metallic structures.

Table 1

| (1) Test piece | (2) Welding method | (3) Welding material | (4) Results of measuring according to this invention — Room temperature diffusible hydrogen | | | (5) Results of measuring according to this invention — Residual hydrogen (extracted at 1000° C) | | (6) I I W method (m/100g) | (7) J I S method (ml/100g) |
|---|---|---|---|---|---|---|---|---|---|
| | | | Weight of deposited metal (g) | Total of measured hydrogen (ml) | ml/100g deposited metal | Measured hydrogen (ml) | ml/100g deposited metal | | |
| HW-70 | Shielded metal arc welding | L80 (H) | 1.72 | 0.0907 | 5.27 | 0.0126 | 0.73 | 2.66 | 1.65 |
| | | | 1.86 | 0.0953 | 5.12 | 0.0132 | 0.71 | 2.13 | 1.73 |
| SM-58 | " | D5826 | 1.93 | 0.1230 | 6.48 | 0.0160 | 0.83 | 5.64 | 3.90 |

Table 1-continued

| (1) Test piece | (2) Welding method | (3) Welding material | (4) Results of measuring according to this invention - Room temperature diffusible hydrogen - Weight of deposited metal (g) | Total of measured hydrogen (ml) | ml/100g deposited metal | (5) Residual hydrogen (extracted at 1000° C) - Measured hydrogen (ml) | ml/100g deposited metal | (6) I I W method (m/100g) | (7) J I S method (ml/100g) |
|---|---|---|---|---|---|---|---|---|---|
| SM-50 | " | D5016(L) | 2.04 | 0.1375 | 6.74 | 0.0173 | 0.85 | 6.61 | 2.43 |
|  |  |  | 1.83 | 0.1153 | 6.31 | 0.0148 | 0.81 | 4.96 | 2.16 |
|  |  |  | 1.85 | 0.1246 | 6.73 | 0.0144 | 0.78 | 5.71 | 3.70 |
| SM-50 | " | D5016(H) | 2.03 | 0.2602 | 12.82 | 0.0248 | 1.22 | 9.73 | 5.90 |
|  |  |  | 2.17 | 0.2743 | 12.63 | 0.0304 | 1.40 | 9.21 | 4.30 |
| SM-50 | " | D5026 | 2.13 | 0.02003 | 9.40 | 0.0220 | 1.03 | 8.32 | 4.80 |
|  |  |  | 1.94 | 0.1874 | 9.66 | 0.0196 | 1.01 | 9.54 | 3.06 |
| SM-50 | " | D5003 | 2.11 | 0.8067 | 38.21 | 0.0414 | 1.96 | 33.5 | 22.7 |
|  |  |  | 2.24 | 0.8775 | 39.12 | 0.0452 | 2.02 | 31.7 | 24.9 |
| SM-41 | " | D4301 | 2.42 | 1.4657 | 60.60 | 0.0735 | 3.03 | 50.5 | 38.4 |
|  |  |  | 2.37 | 1.4509 | 61.32 | 0.0761 | 3.21 | 53.0 | 36.0 |
| HW-70 | " | L80 (L) | 1.90 | 0.1024 | 5.39 | 0.0137 | 0.72 | 2.73 | 1.82 |
|  |  |  | 1.98 | 0.1017 | 5.14 | 0.0160 | 0.81 | 2.17 | 2.56 |
| HW-70 | MIG* welding | Micro-wire for 80K use | 1.10 | 0.0176 | 1.60 | 0.0072 | 0.65 | (1.32)* | (tr)* |
|  |  |  | 1.06 | 0.0174 | 1.64 | 0.0064 | 0.60 | (1.78)* | (tr)* |

*The measuring of hydrogen in the deposited metal in MIG welding is not regulated both in I I W method and J I S method.

Table 2

|  |  | Method of this invention | | I I W method | J I S method |
|---|---|---|---|---|---|
|  |  | Room temperature diffusible hydrogen | High temperature (1000° C) heat-extracted hydrogen | | |
| Accuracy of reproduction (ml/100g) σ (=R/d₂) | ml/100g $H_2 \geq 20$ | 0.73 | — | 1.91 | 2.04 |
|  | $20 > H_2 \geq 5$ | 0.23 | — | 0.99 | 1.42 |
|  | $5 > H_2$ | 0.05 | 0.06 | 0.46 | 0.99 |
| Detection limit in gas volume | (ml) | 0.00001 | 0.00001 | 0.05 | 0.05 |
| Weight of deposited metal | (g) | about 1 – 2 | about 1 – 2 | about 1 – 2 | about 20 |
| Detection limit in gas volume per 100 g of deposited metal | (ml/100g) | 0.005 | 0.005 | 2.5 | 0.25 |
| Lower limit ($\geq 2\sigma$) for quantitative measuring taking into account the reproducibility | (ml/100g) | 0.1 | 0.12 | 2.5 | 2.0 |

Table 3

| Test piece | A | B | C | D | E | F |
|---|---|---|---|---|---|---|
| Hydrogen charging time (minute) | 1 | 5 | 10 | 50 | 100 | 500 |
| Total amount of diffusible hydrogen (ml) | 0.00056 | 0.00244 | 0.00434 | 0.0218 | 0.0429 | 0.2171 |
| (ml/100g) | 0.008 | 0.035 | 0.062 | 0.311 | 0.614 | 3.10 |

Table 4

| Test piece | | Lapse of time (hr) | 1 | 5 | 10 | 48 |
|---|---|---|---|---|---|---|
| D | Amount of hydrogen collected (ml/10 minutes) | | 0.00018 | 0.00012 | 0.00008 | 0.00002 |
|  | Amount of hydrogen per unit time per 100 g (ml/100 g · hr) | | 0.0155 | 0.0103 | 0.0069 | 0.0017 |
| F | Amount of hydrogen collected (ml/5 minutes) | | 0.00094 | 0.00065 | 0.00042 | 0.00013 |
|  | Amount of hydrogen per unit time per 100g (ml/100g · hr) | | 0.1612 | 0.1131 | 0.0724 | 0.0222 |

Table 5

| (1) Test piece | (2) Welding method | (3) Welding material | (4) Results of measuring according to this invention - Room-temperature diffusible hydrogen ml/100g deposited metal | (5) 500° C discharged hydrogen ml/100g deposited metal | (6) 1000° C discharged hydrogen ml/100g deposited metal | (7) melt-discharged hydrogen ml/100g deposited metal | (8) IIW method ml/100g | (9) JIS method ml/100g |
|---|---|---|---|---|---|---|---|---|
| HW-70 | Shielded metal are welding | L80(H) | 5.16 | 0.52 | 0.23 | 0.10 | 2.84 | 1.43 |
|  |  |  | 5.03 | 0.51 | 0.22 | 0.09 | 2.27 | 2.12 |
| HW-70 | " | L80(L) | 5.27 | 0.51 | 0.20 | 0.09 | 2.57 | 1.56 |
|  |  |  | 5.05 | 0.57 | 0.18 | 0.08 | 2.14 | 1.37 |
| SM-50 | " | D5016(L) | 6.42 | 0.55 | 0.19 | 0.08 | 4.72 | 2.16 |
|  |  |  | 6.62 | 0.51 | 0.23 | 0.10 | 5.21 | 3.74 |
| HW-70 | MIG* welding | Micro-wire for 80K use | 1.70 | 0.40 | 0.18 | 0.07 | (1.31)* | (tr)* |
|  |  |  | 1.65 | 0.38 | 0.16 | 0.06 | (1.20)* | (tr)* |

*The measuring of hydrogen in the deposited metal in MIG welding is not regulated both in IIW method Table 5-continued

| (1) | (2) | (3) | (4) | (5) | (6) | (7) | (8) | (9) |
|---|---|---|---|---|---|---|---|---|
|  | and JIS method. |  |  |  |  |  |  |  |

Table 6

|  | Room temperature diffusible hydrogen | This invention | | | IIW method | JIS method |
|---|---|---|---|---|---|---|
|  |  | 500° C discharged hydrogen | 1000° C discharged hydrogen | Melt-discharged hydrogen | | |
| reproducibility (ml/100g) $\sigma(=R/d_2)$ | 0.13 | 0.029 | 0.020 | 0.010 | 0.35 | 0.72 |
| Detection limit in gas volume (ml) | 0.00001 | same as left | same as left | same as left | 0.05 | 0.05 |
| Weight of deposited metal (g) | about 1 – 2 | same as left | same as left | same as left | about 1 – 2 | about 20 |
| Detection limit in gas volume per 100g deposited metal (ml/100g) | 0.005 | same as left | same as left | same as left | 2.5 | 0.25 |
| Lower limit ($\geq 2\sigma$) for quantitative measuring taking into account the reproducitibity (ml/100g) | 0.3 | 0.06 | 0.04 | 0.02 | 2.5 | 1.4 |

We claim:

1. In a method for automatically and quantitatively measuring hydrogen gas in a metal consisting essentially of the steps of introducing test pieces into a plurality of hydrogen collectors provided with valves at the inlet and outlet thereof and arranged in a system for quantitatively measuring hydrogen through which a carrier gas is continuously passed; maintaining the test pieces in the hydrogen collectors for a predetermined time so as to discharge hydrogen gas therefrom; feeding the hydrogen gas alternately from the hydrogen collectors to a gas analyzing unit by means of the carrier gas to quantitatively measure the hydrogen, while controlling the amount of gas flow by means of a valve which controls the amount of carrier gas flow; and recording the results of the quantitative measurement by means of an integrator, the improvement which comprises carrying out the discharge of the hydrogen at ordinary temperatures; allowing the carrier gas to by-pass the hydrogen collectors by closing the inlet and outlet valves of each of the hydrogen collectors for said predetermined time; repeating the quantitative measurement concerning each of the test pieces for a number of times sufficient to accurately measure the rate of discharge of the hydrogen from the test pieces per unit time as well as the total amount of hydrogen accumulated in the hydrogen collector; predetermining a program of the times per each quantitative measurement cycle, the number of the cycle, the timing of the valves operations, the timing of the operation of the gas analyzing unit and the timing of operation of the integrator by a sequence control mechanism; and conducting the valves operations, the operation of the gas analyzing unit and the operation of the integrator by the sequence control mechanism.

2. A method according to claim 1, in which the hydrogen collectors containing the test piece are heated to a predetermined temperature after the collectors are degassed by a vacuum pump.

3. In a method for automatically and quantitatively measuring hydrogen gas in a metal consisting essentially of the steps of introducing test pieces into a plurality of hydrogen collectors provided with valves at the inlet and outlet thereof and arranged in a system for quantitatively measuring hydrogen through which a carrier gas is continuously passed; maintaining the test pieces in the hydrogen collectors for a predetermined time so as to discharge hydrogen gas therefrom; feeding the hydrogen gas alternately from the hydrogen collectors to a gas analyzing unit by means of the carrier gas to quantitatively measure the hydrogen gas, while controlling the amount of flow of the carrier gas by means of a control valve; memorizing the amount of the hydrogen measured in every analyzing cycle in order and calculating the lapse time change of the discharging rate of each test piece and the accumulated amount of the hydrogen per test piece; and recording the results of the quantitative measurement by means of an integrator, the improvement which comprises carrying out the discharge of the hydrogen at ordinary temperatures; allowing the carrier gas to by-pass the hydrogen collectors by closing the inlet and outlet valves of each of the hydrogen collectors for said predetermined time; repeating the quantitative measurement concerning each of the test pieces for a number of times sufficient to accurately measure the rate of discharge of the hydrogen from the test pieces per unit time as well as the total amount of hydrogen accumulated in the hydrogen collector; predetermining a program of the time per each quantitative measurement cycle, the number of the cycle; the timing of the valves operations, the timing of operation of the gas analyzing unit, the process of the memorization and the calculation, and the timing of the operation of the integrator by means of a computer control; and conducting the valves operations, the operation of the gas analyzing unit, the process of the memorization and the calculation, the operation of the integrator in accordance with the program by means of the computer control.

4. A method according to claim 3, in which the hydrogen collectors containing the test piece are heated to a predetermined temperature after the collectors are degassed by a vacuum punp.

* * * * *

UNITED STATES PATENT AND TRADEMARK OFFICE
CERTIFICATE OF CORRECTION

PATENT NO. : 4,142,399

DATED : March 6, 1979

INVENTOR(S) : Hideshi SATO; Takashi OTSUBO; Syunsuke GOTO; Minoru AMANO; and Naoyuki SERIU It is certified that error appears in the above—identified patent and that said Letters Patent is hereby corrected as shown below:

Title page, line designated "[73] Assignee:", change

"Nippon Steel Corporation, Tokyo, Japan" to

-- Nippon Steel Corporation; Japan Analyst Corporation, both of Tokyo, Japan --

Signed and Sealed this

Twelfth Day of July 1983

[SEAL]

Attest:

GERALD J. MOSSINGHOFF

Attesting Officer

Commissioner of Patents and Trademarks